United States Patent [19]

Strohmaier et al.

[11] Plant 5,231

[45] May 15, 1984

[54] PLUM TREE, "ALETA ROSE"

[76] Inventors: Loretta J. Strohmaier, 9162 Ave. 392, executrix; Phillip D. Strohmaier, 39252 Rd. 88, both of Dinuba, Calif. 93618; Alfred W. Strohmaier, deceased, late of Dinuba, Calif.

[21] Appl. No.: 437,746

[22] Filed: Oct. 29, 1982

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree generally similar to the Simka variety of plum tree (U.S. Plant Pat. No. 1,882) but distinguished by bearing fruit which ripens about ten days earlier and which has a 90 to 100 percent red-purple skin coloration.

1 Drawing Figure

BACKGROUND OF THE VARIETY

The present invention relates to a new and distinct variety of plum tree which is nearly identical in tree and fruit characteristics to the Simka variety of plum tree (U.S. Plant Pat. No. 1,882), but which is distinguished from the Simka variety by bearing fruit which ripens about 10 days earlier and which has a more extensive skin coloration. The new variety has been named "Aleta Rose" for commercial marketing.

The Simka variety of plum tree is extensively planted for commerical plum production due to its vigorous growth, its tendency to self-thinning, its bearing of large fruit which are attractively and extensively colored and which remain in a marketable condition for protracted periods when left on the tree after coloring. An important factor in the sale of fresh fruit is uniform and attractive coloration, the Simka variety being desirable in that one-half to three-quarters of each plum has a dark purple skin color when fully ripe. The subject new variety produces fruit which is even more extensively colored.

As with all produce, the time of harvest of plums greatly influences the price brought on the market, fruit which can be marketed earlier usually commanding a higher price. It is, therefore, desirable to provide a plum tree bearing fruit which has the desirable characteristics of fruit borne by the Simka variety and which ripens substantially earlier. It is, of course, even more desirable to provide a variety of plum tree bearing such earlier ripening fruit which has a 90 to 100 percent dark purple coloration.

ORIGIN AND ASEXUAL REPRODUCTION OF THE NEW VARIETY

The subject variety of plum tree was discovered in 1977 by Alfred W. Strohmaier, deceased, as a mutation involving a single scaffold limb in a commercial bearing orchard of plum trees of the Simka variety (U.S. Plant Pat. No. 1,882) located at 9162 Avenue 392, near the City of Dinuba, in the County of Tulare, in the State of California. The new variety was asexually reproduced by budding in May 1980 under the direction of Loretta J. Strohmaier and Phillip D. Strohmaier, respectively, the widow and son of said Alfred W. Strohmaier. The resulting trees were planted in such orchard and bore fruit in 1982, the tree and fruit characteristics resulting from such asexual reproduction proving identical to those of the original mutation.

SUMMARY OF THE NEW VARIETY

The instant variety of plum tree is characterized by perpetuating the general tree and fruit characteristics of the Simka variety of plum tree (U.S. Plant Pat. No. 1,882) of which it is a mutation, but has the important distinction of bearing fruit which ripens approximately ten days earlier than fruit of the Simka variety under the growing conditions prevailing in the San Joaquin Valley of California and which as a completely, or nearly completely, dark purple skin coloration when fully ripe. The fruit of the instant variety is semi-freestone and has yellow flesh.

BRIEF DESCRIPTION OF THE DRAWING

The accompanying drawing is a color photograph of three mature plums of the subject variety, two of the plums being attached to a representative branch bearing characteristic leaves and the other plum being divided substantially in the sucture plane to show the flesh and stone characteristics.

DETAILED DESCRIPTION

Referring more particularly to the pomological details of the new and distinct variety of plum tree, the following has been observed under the ecological conditions prevailing in the above-specified orchard near Dinuba, Tulare County, Calif. All of the color plate distinctions are by reference to the Maerz and Paul *Dictionary of Color,* Second Edition, 1950, common descriptive color names also being used.

TREE

Size: Large.

Figure: Upright to spreading with shade and density determined by pruning.

Vigor: Vigorous; hardy for California growing conditions.

Bearing: Productive and regular, bagging tests indicate the new variety to be partially self-fertile.

Trunk: Average diameter for species and of average surface texture.

Branches: Medium size and surface texture.

Leaves: Large size and moderately thick.

*Length.*—145 mm.

*Width.*—67 mm.

*Shape.*—Generally obovate with apex acute to cuspidate.

*Margin.*—Finely crenate and not wavy.

*Petiole.*—Moderately long, 10 to 14 mm, green (19-J-6) and 2 mm thick at base.

*Glands.*—Three to five small globose glands at leaf base with one to two more occasionally on petiole.

*Color.*—Upper surface dark green (24-L-9), lower surface lighter green (23-H-7).

*Stipules.*—Greenish (22-F-6), deeply serrate and persistent on many petioles.

Flowers:

*Date of bloom.*—Medium to late in relation to other plum varieties, last week of February to first week of March.

*Size.*—Medium.

*Color.*—White.

FRUIT (Described at full to slightly past commercial maturity.)

Maturity: In 1982, first pick June 25 and last pick June 29.

Size: Uniform, medium to large, average axial diameter 50 mm, average suture diameter 53 mm, average cheek diameter 57 mm.

Form: Uniform, symmetrical, globose in axial aspect, globose to slightly cordate in ventral suture aspect.

Suture: A distinct narrow and shallow line extending from base to apex. Color of suture blends in with rest of fruit at maturity. Noticeably free of flecking along suture line.

Ventral surface: Rounded, not noticeably lipped.

Stem cavity: Rounded, oval to nearly circular in axial aspect. Moderate depth 9 to 10 mm. Width 7 to 8 mm; length 8 to 9 mm.

Base: Rounded to slightly truncate, usually at right angle to fruit axis.

Apex: Rounded, pistil point apical and inconspicuous.

Stem: Medium length 9–12 mm in length, 2 mm in thickness. Greenish brown color (21-I-2) to brown (16-L-10) in color.

Skin: Medium thickness; medium texture; no tendency to crack observed in original tree; slightly acid; tenacious to flesh; color: purple-red (7-L-4) to purple (8-L-5) over 90 to 100 percent of fruit surface; pubescence lacking; moderate to heavy grey bloom over entire surface; numerous yellow flecks over both cheeck surfaces.

Flesh color: Yellow-amber (11-J-32) with no red streaking or bleeding in from skin; surface of pit cavity slightly darker (11-K-3).

Texture: Firm, fine, meaty, crisp, moderately juicy.

Fibers: Few, tender.

Ripening: Even.

Aroma: Very slight.

Flavor: Good, slightly acid.

Eating quality: Good.

Stone: Semi-free, breaks relatively free from flesh; at times flesh and fibers cling along dorsal suture of stone; no observed tendency to crack.

*Size.*—Medium.

*Average length.*—22 mm.

*Average width.*—18 mm.

*Average thickness.*—7 to 10 mm.

*Form.*—Generally oval, although at times heavily eroded on dorsal suture near the base.

*Base.*—Slightly oblique to dorsal suture.

*Apex.*—Rounded.

*Sides.*—Equal, some shallow grooving of basal area, in lateral aspect.

*Color.*—Buff (11-J-5).

Use: A fresh shipping variety for both local and long distance.

Keeping quality: Good.

Shipping quality: Good.

Resistance to disease and insects: Average, no particular susceptibility observed.

Although the new variety of plum tree possesses the described characteristics as a result of the growing conditions prevailing in Tulare County, Calif. in the San Joaquin Valley, it is to be understood that variations of the usual magnitude in characteristics incident to growing conditions, fertilization, pruming and pest control are to be expected.

Having thus described and illustrated the new variety of plum tree, what is claimed is:

1. A new and distinct variety of plum tree, substantially as illustrated and described, characterized by similarity in tree and fruit characteristics to the Simka variety of plum tree (U.S. Plant Pat. No. 1,882), but distinguished therefrom and characterized as to novelty by bearing fruit which ripens approximately ten days earlier than fruit of the Simka variety and which, when ripe, has a 90 percent to full red-purple skin coloration.

* * * * *

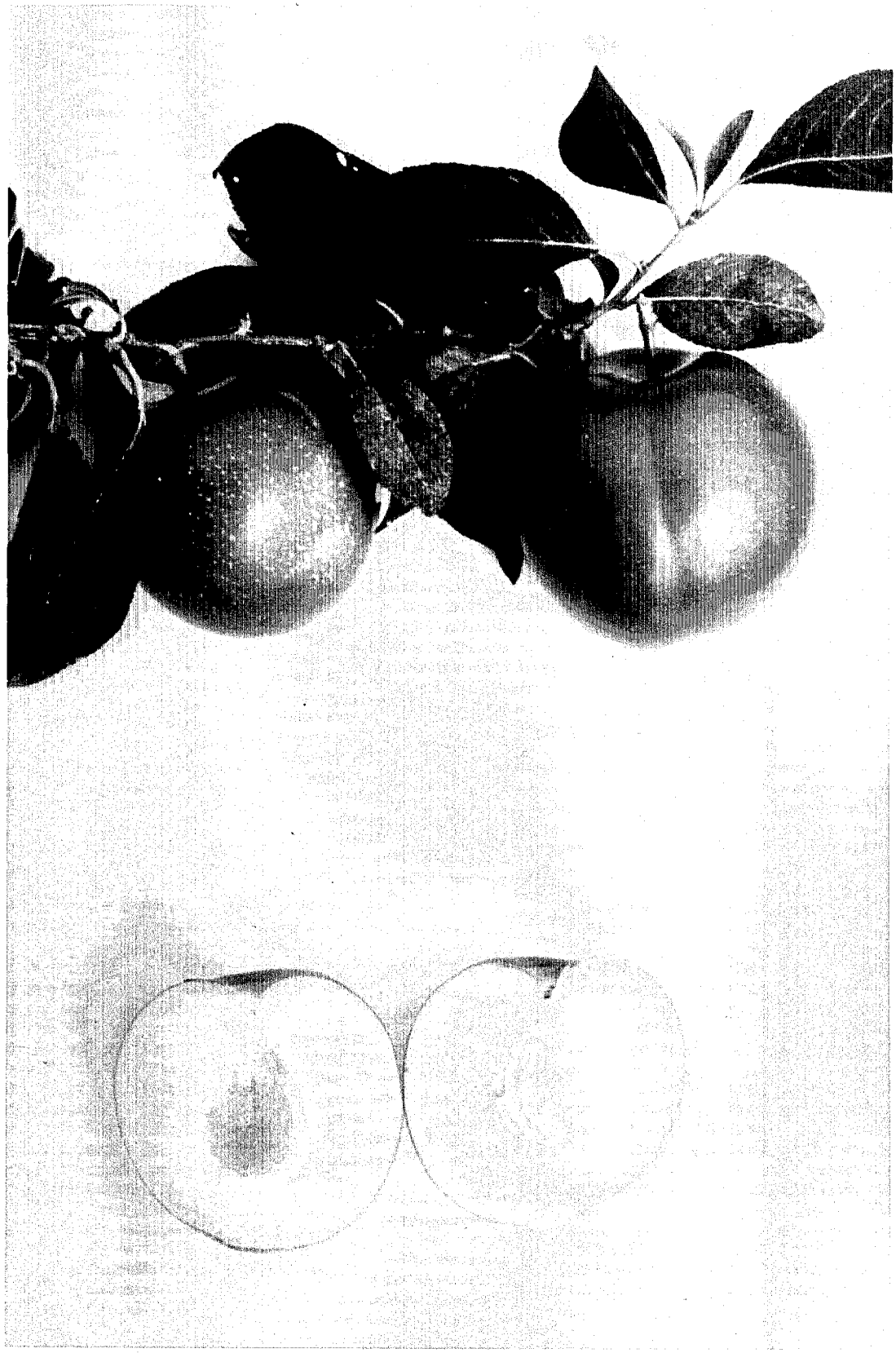

UNITED STATES PATENT AND TRADEMARK OFFICE

CERTIFICATE OF CORRECTION

PATENT NO. : PP 5,231

DATED : May 15, 1984

INVENTOR(S) : Loretta J. Strohmaier; Philip D. Strohmaier; and Alfred W. Strohmaier, deceased It is certified that error appears in the above-identified patent and that said Letters Patent is hereby corrected as shown below:

Column 2, Line 21, delete "sucture" and substitute

---suture---,

Column 4, Line 3, delete "(11-J-32)" and substitute

---(11-J-2)---,

Column 4, Line 38, delete "pruming" and substitute

---pruning---.

Signed and Sealed this

*Ninth* Day of *October 1984*

[SEAL]

*Attest:*

GERALD J. MOSSINGHOFF

*Attesting Officer*

*Commissioner of Patents and Trademarks*